United States Patent [19]
Sohda et al.

[11] Patent Number: 5,489,602
[45] Date of Patent: Feb. 6, 1996

[54] THIAZOLIDINEDIONE DERIVATIVES, THEIR PRODUCTION AND USE

[75] Inventors: Takashi Sohda, Takatsuki; Hitoshi Ikeda, Higashiosaka; Sachiko Imai, Kyoto; Yu Momose, Takarazuka, all of Japan

[73] Assignee: Takeda Chemical Industries, Ltd., Osaka, Japan

[21] Appl. No.: 376,529

[22] Filed: Jan. 23, 1995

Related U.S. Application Data

[62] Division of Ser. No. 171,694, Dec. 22, 1993, abandoned.

[30] Foreign Application Priority Data

Dec. 28, 1992 [JP] Japan .................................. 4-348568
Jul. 22, 1993 [JP] Japan .................................. 5-180996

[51] Int. Cl.$^6$ .................... C07D 417/14; A61K 31/44
[52] U.S. Cl. ...................... 514/340; 546/276; 546/256; 546/193; 546/280; 544/124; 514/342; 514/333; 514/318; 514/237.2
[58] Field of Search ...................... 546/276, 256, 546/193; 514/340, 333, 318, 237.2, 342; 544/124

[56] References Cited

U.S. PATENT DOCUMENTS 4,725,610  2/1988  Meguro et al. .......................... 514/369
4,775,687 10/1988  Meguro et al. .......................... 514/369

FOREIGN PATENT DOCUMENTS 0332332  9/1989  European Pat. Off. .
64586  11/1978  Japan .

OTHER PUBLICATIONS

Sohda et al., Chemical Abstracts, vol. 117, No. 5, 3 Aug., 1992 Abstract No. 48397w.
Grant & Hackh's Chemical Dictionary McGraw–Hill Book Co. 1990 p. 22.
Sohda et al. Chem. Pharm. Bull. 30(10) pp. 3580–3600, 1982.

*Primary Examiner*—Jane Fan
*Attorney, Agent, or Firm*—Wenderoth, Lind & Ponack

[57] ABSTRACT

The object of the present invention is to provide a new thiazolidinedione derivative exhibiting excellent hypoglycemic and hypolipidemic action.

Thiazolidinedione derivative represented by the general formula:

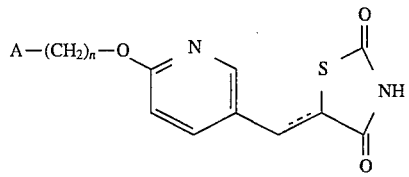

wherein n represents an integer from 1 to 3; A represents an aromatic 5-membered heterocyclic ring residue which has at least one nitrogen atom as a ring component atom, which is bound via a carbon atom adjacent to the nitrogen atom and which may be substituted; ••••••• is a single bond or a double bond, or pharmacologically acceptable salt thereof, is novel, and shows excellent hypoglycemic and hypolipidemic action.

6 Claims, No Drawings

THIAZOLIDINEDIONE DERIVATIVES, THEIR PRODUCTION AND USE

This application is a division of application Ser. No. 08/171,694, filed Dec. 22, 1993 (now abandoned).

The present invention relates a new thiazolidinedione derivative possessing hypoglycemic and hypolipidemic activity and a diabetic remedy containing it, both for pharmaceutical use.

Traditionally, various biguanide compounds and sulfonylurea compounds have been used as diabetic remedies. However, biguanide compounds are hardly used at present, since they cause lactic acidosis, while sulfonylurea compounds, with their potent hypoglycemic action, often cause severe hypoglycemia, requiring special attention in use. There are thiazolidinedione derivatives known to possess hypoglycemic and hypolipidemic activity free or such drawbacks.

For example, Japanese Patent Examined Publication No. 57635/1987 describes a series of 5-[(2-alkoxy-5-pyridyl)methyl]-2,4-thiazolidinedione derivatives as having a (substituted-3-pyridyl)methyl group at the 5-position.

The present inventors investigated 5-[(substituted-3-pyridyl)methyl]- 2,4-thiazolidinedione derivatives, which possess potent hypoglycemic and hypolipidemic activity, and found that their activity is markedly enhanced by introducing as a substituent for the pyridine ring an alkoxy group having an aromatic 5-membered heterocyclic ring residue which contains at least one nitrogen atom as a ring component atom, which binds via a carbon atom adjacent to the nitrogen atom and which may be substituted.

Accordingly, the present invention comprises:

1. a thiazolidinedione derivative represented by the general formula:

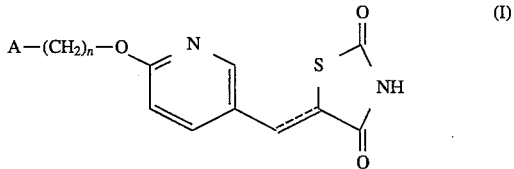

wherein n represents an integer from 1 to 3; A represents an aromatic 5-membered heterocyclic ring residue which has at least one nitrogen atom as a ring component atom, which is bound via a carbon atom adjacent to the nitrogen atom and which may be substituted; ......... is a single bond or double bond, or pharmacologically acceptable salt thereof.

2. a pharmaceutical composition containing as an active ingredient a thiazolidinedione derivative represented by general formula (I) or pharmacologically acceptable salt thereof, and 3. a method of producing a thiazolidinedione derivative represented by general formula:

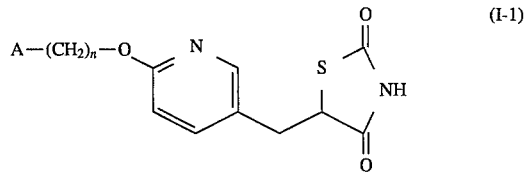

wherein the symbols have the same definitions as above, characterized by hydrolysis of an iminothiazolidinone compound represented by the general formula:

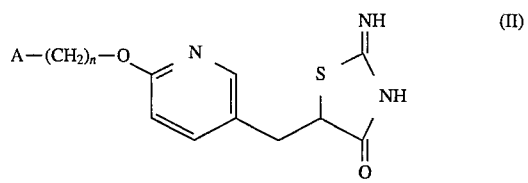

wherein the symbols have the same definitions as above.

4. A method of producing a thiazolidinedione derivative represented by the general formula (I) characterized by condensation of a compound represented by the general formula:

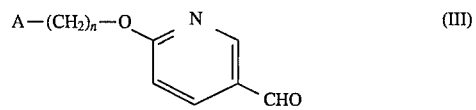

wherein the symbols have the same definitions as above, and 2,4-thiazolidinedione and, if necessary reducing the resulting compound.

With respect to the above general formulas (I), (I-1), (II) and (III), n is preferably the integer 2 or 3, though varying from 1 to 3.

The compound represented by general formula (I) wherein ········ is a single bond is specifically represented by general formula (I-1), and the compound represented by the general formula (I) wherein ········ is a double bond is specifically represented by the general formula:

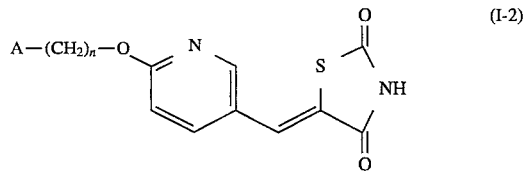

wherein the symbols have the same definitions as above. Concerning compounds of general formula (I), those having a single bond at the moiety indicated by ········ in general formula (I) are preferred.

With respect to the above general formulas (I), (I-1), (I-2), (II) and (III), the aromatic 5-membered heterocyclic ring residue for A is defined as follows: ① It is a 5-membered ring. ② It is a heterocyclic ring having at least one nitrogen atom as a ring component atom. ③ It may have two or more nitrogen atoms and hetero atoms other than nitrogen such as atoms of oxygen and sulfur, as ring component atoms. ④ The ring is an aromatic ring having an unsaturated bond. ⑤ It is a group bound via a carbon atom adjacent to a nitrogen atom. ⑥ It may be substituted at any position on the ring thereof. This aromatic 5-membered heterocyclic ring residue for A is exemplified by pyrrolyl (2-pyrrolyl), pyrazolyl (3-pyrazolyl), imidazolyl (2-imidazolyl, 4-imidazolyl), triazolyl (1,2,3-triazol-4-yl, 1,2,4-triazol-3-yl), tetrazolyl, oxazolyl (2-oxazolyl, 4-oxazolyl) and thiazolyl (2-thiazolyl, 4-thiazolyl).

This aromatic 5-membered heterocyclic ring residue may have one or more substituents at any positions on the ring thereof. Such substituents are exemplified by hydrocarbon residues and heterocyclic ring residues, which may have their own substituents.

Such hydrocarbon residues include aliphatic hydrocarbon residues, alicyclic hydrocarbon residues, alicyclic-aliphatic hydrocarbon residues, aryl-aliphatic hydrocarbon residues and aromatic hydrocarbon residues. Such aliphatic hydrocarbon residues include those having 1 to 8 carbon atoms, specifically saturated aliphatic hydrocarbon residues having 1 to 8 carbon atoms such as methyl, ethyl, propyl, isopropyl, butyl, isobutyl, sec-butyl, tert-butyl, pentyl, isopentyl, neopentyl, tert-pentyl, hexyl, isohexyl, heptyl and octyl and unsaturated aliphatic hydrocarbon residues having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl. Such alicyclic hydrocarbon residues include those having 3 to 7 carbon atoms, specifically saturated alicyclic hydrocarbon residues having 3 to 7 carbon atoms such as cyclopropyl, cyclobutyl, cyclopentyl, cyclohexyl and cycloheptyl and unsaturated alicyclic hydrocarbon residues having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. Such alicyclic-aliphatic hydrocarbon residues include those resulting from binding of above-mentioned alicyclic hydrocarbon residues and above-mentioned aliphatic hydrocarbon residues to have 4 to 9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl. Such aryl-aliphatic hydrocarbon residues include phenylalkyls having 7 to 9 carbon atoms such as benzyl, phenethyl, 1-phenylethyl, 3-phenylpropyl, 2-phenylpropyl and 1-phenylpropyl, and naphthylalkyls having 11 to 13 carbon atoms such as α-naphthylmethyl, α-naphthylethyl, β-naphthylmethyl and β-naphthylethyl. Such aromatic hydrocarbon residues include phenyl and naphthyl (α-naphthyl, β-naphthyl).

The above-described heterocyclic ring residue is a 5- or 6-membered ring group which contains 1 to 3 non-carbon atoms selected from atoms of N, O and S as ring component atoms and which is bound via carbon. Such heterocyclic ring residues include aromatic heterocyclic ring residues such as thienyl (2-thienyl, 3-thienyl), furyl (2-furyl, 3-furyl), pyridyl (2-pyridyl, 3-pyridyl, 4-pyridyl), thiazolyl (2-thiazolyl, 4-thiazolyl, 5-thiazolyl) and oxazolyl (2-oxazolyl, 4-oxazolyl, 5-oxazolyl), and saturated heterocyclic ring residues such as piperidinyl (2-piperidinyl, 3-piperidinyl, 4-piperidinyl), pyrrolidinyl (2-pyrrolidinyl, 3-pyrrolidinyl), morpholinyl (2-morpholinyl, 3-morpholinyl) and tetrahydrofuryl (2-tetrahydrofuryl, 3-tetrahydrofuryl).

The above-described hydrocarbon residue or heterocyclic ring residue may be substituted at any position. When the hydrocarbon residue contains an alicyclic residue or when it is a saturated heterocyclic ring residue, it may have 1 to 3 lower alkyl groups having 1 to 3 carbon atoms (e.g., methyl, ethyl, propyl, isopropyl) on the ring thereof (including N atoms). When the hydrocarbon residue contains an aromatic hydrocarbon residue or when it is an aromatic heterocyclic ring residue, it may have 1 to 4 substituents, whether identical or not, on the ring thereof (not including hetero atoms). Examples of these substituents include halogens (fluorine, chlorine, iodine), hydroxy, cyano, trifluoromethyl, lower alkoxy groups (e.g., those having 1 to 4 carbon atoms such as methoxy, ethoxy, propoxy, isopropoxy and butoxy), lower alkyl groups (e.g., those having 1 to 4 carbon atoms such as methyl, ethyl, propyl, isopropyl and butyl), lower alkoxycarbonyl groups (e.g., those having 2 to 4 carbon atoms such as methoxycarbonyl, ethoxycarbonyl and propoxycarbonyl) and lower alkylthio groups (e.g., those having 1 to 3 carbon atoms such as methylthio, ethylthio, propylthio and isopropylthio).

When the aromatic 5-membered heterocyclic ring residue represented by A has two or more hydrocarbon residues as substituents therefor, which hydrocarbon residues are located at mutually adjacent positions on the aromatic 5-membered heterocyclic ring, they may bind together to form a condensed ring. This means that the two hydrocarbon residues bind together to form a saturated or unsaturated di-linear hydrocarbon residue having 3 to 5 carbon atoms. Such linear hydrocarbon residues include —CH$_2$CH$_2$CH$_2$—, —CH$_2$CH$_2$CH$_2$CH$_2$—, —CH$_2$CH$_2$CH$_2$CH$_2$CH$_2$—, —CH=CHCH$_2$—, —CH=CHCH= CH—, —CH=CH—CH=CH—CH$_2$— and —CH=CH—CH$_2$CH$_2$CH$_2$—.

Of the aromatic 5-membered heterocyclic ring residues represented by A, preference is given to the thiazolyl or oxazolyl represented by the formula:

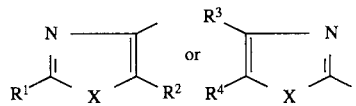

wherein R$^1$ represents hydrogen or a hydrocarbon residue or heterocyclic ring residue which may be substituted; R$^2$ represents hydrogen or a lower alkyl group which may be substituted by a hydroxyl group; R$^3$ and R$^4$ independently represent hydrogen or a hydrocarbon residue which may be substituted, and R$^3$ and R$^4$ may bind together to form a condensed ring; X represents an oxygen atom or a sulfur atom. The hydrocarbon residue and heterocyclic ring residue represented by R$^1$ and substituents therefor are exemplified by the same hydrocarbon residues, heterocyclic ring residues and substituents therefor as specified above for the aromatic 5-membered heterocyclic ring residue.

The lower alkyl group represented by R$^2$ is exemplified by alkyl groups having 1 to 5 carbon atoms such as methyl, ethyl, propyl, isopropyl, butyl, isobutyl, sec-butyl, tert-butyl and pentyl, with preference given to those having 1 to 3 carbon atoms. Although these alkyl groups may have a hydroxyl group at any position, the α-position is preferred.

The hydrocarbon residue represented by R$^3$ or R$^4$ and substituents therefor are exemplified by the same hydrocarbon residues and substituents therefor as specified above for the aromatic 5-membered heterocyclic ring residue. R$^3$ and R$^4$ may bind together to form a condensed ring, which is the same as the condensed ring formed by an aromatic 5-membered heterocyclic ring residue having two hydrocarbon residues as substituents at mutually adjacent positions.

The thiazolidinedione derivative represented by general formula (I) is a compound having acidic nitrogen and a pyridine ring on the thiazolidine ring thereof, involving basic and acidic salts. Example basic salts of thiazolidinedione derivative (I) include metal salts such as sodium salt, potassium salt, aluminum salt, magnesium salt and calcium salt. Example acidic salts include inorganic acid salts such as hydrochloride, sulfate and hydrobromide, and organic acid salts such as methanesulfonate and tartrate.

Compound (I) or pharmacologically acceptable salt thereof of the present invention exhibits hypoglycemic action and can be used as such or in a composition with a known pharmacologically acceptable carrier, excipient, filler and other additives in mammals, including humans, as a diabetic remedy. Compound (I) or pharmacologically acceptable salt thereof of the present invention also exhibits improving activity of insulin resistance and can also be used as a hypotensor.

Compound (I) of the present invention has low toxicity. For example, when the compound of Example 1 was orally administered to mice at 15 mg/kg for 4 days, no changes occurred in body weight or liver weight, in comparison with control. When each of the compounds produced in Examples 2, 5 and 6 was administered orally at 100 mg/kg or intraperitoneally at 50 mg/kg, no deaths occurred.

Concerning the method of administration, compound (I) of the present invention is normally used orally in the form of tablets, capsules (including soft capsules and microcapsules), powders, granules and other forms, but as the case may be it can be non-orally administered in the form of injectable preparations, suppositories, pellets and other forms. Single dose is 0.05 to 10 mg/kg for oral administration in adults, preferably 1 to 3 times daily.

Process for production of compound (I) of the present invention is described below.

Compound (I-1) can be produced by hydrolysis of compound (II). Usually, hydrolysis of compound (II) is carried out in an appropriate solvent in the presence of water and mineral acid. Such solvents include alcohols (e.g., methanol, ethanol, propanol, 2-propanol, butanol, isobutanol, 2-methoxyethanol), dimethylsulfoxide, sulfolane and mixtures thereof. Mineral acids include hydrochloric acid, hydrobromic acid and sulfuric acid, the amount of its use being 0.1 to 20 mol, preferably 0.2 to 10 mol per mol of compound (II). Water is added in excess relative to compound (II). This reaction is normally carried out under warming or heating conditions, normal reaction temperature being 60° to 150° C. Heating time is normally several hours to ten and several hours.

Thiazolidinedione derivative (I) or salt thereof thus obtained can be isolated and purified by known means of separation and purification such as ordinary concentration, concentration under reduced pressure, crystallization, recrystallization, re-dissolution and chromatography.

Iminothiazolidinone (II), used as a starting material for the present method, can, for example, be produced as follows:

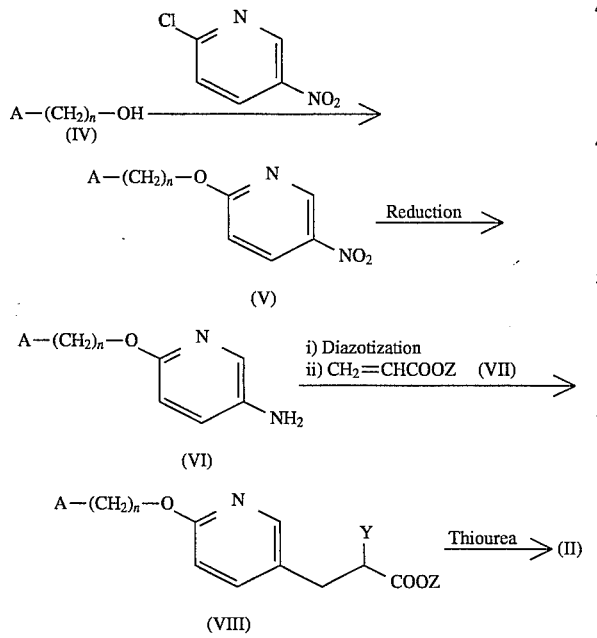

In the above reaction scheme, Y in formula (VIII) represents a halogen atom such as chlorine, bromine or iodine; Z in formulas (VII) and (VIII) represents a hydrogen atom or a lower alkyl group having 1 to 4 carbon atoms such as methyl, ethyl, propyl, isopropyl, butyl or isobutyl; the other symbols have the same definitions as above.

The reaction of compound (IV) to compound (V) is carried out by condensing compound (IV) and 2-chloro-5-nitropyridine in the presence of, for example, sodium hydride. This reaction can be carried out in a solvent such as N,N-dimethylformamide, dioxane, tetrahydrofuran or dimethylsulfoxide at −20° to 60° C. Next, the reaction of compound (V) to compound (VI) can easily be carried out by catalytically reducing compound (V) by a conventional method with, for example, palladium-carbon as a catalyst, or by reducing compound (V) by a conventional method with zinc or iron and acetic acid. Compound (VI) may be isolated as a pure product or may be subjected to the reaction in the next process without isolation or purification. The reaction of compound (VI) to compound (VIII) can be carried out by Meerwein arylation, wherein compound (VI) is diazotized in the presence of hydrogen halide (HY) and then reacted with acrylic acid or ester thereof (VII) in the presence of a copper catalyst (e.g., cuprous oxide, cupric oxide, cuprous chloride, cupric chloride, cuprous bromide, cupric bromide). Compound (VIII) may be purified by chromatography etc., but may be subjected to the reaction in the next process without isolation or purification.

Compound (VIII) may be then reacted with thiourea to yield compound (II). This reaction is carried out normally in a solvent such as an alcohol (e.g., methanol, ethanol, propanol, 2-propanol, butanol, isobutanol, 2-methoxyethanol), dimethylsulfoxide, N,N-dimethylformamide or sulfolane. Reaction temperature is normally 20° to 180° C., preferably 50° to 150° C. The amount of thiourea used is 1 to 2 mol per mol of compound (VIII). As this reaction proceeds, hydrogen halide occurs as a byproduct; to trap this, a deacidifying agent such as sodium acetate or potassium acetate may be added. The amount of deacidifying agent used is normally 1 to 1.5 mol per mol of compound (VIII). These reactions eventually produce compound (II), which may be isolated as desired, but the acid hydrolysis process of the present invention may be proceeded to immediately without isolation of compound (II).

Alcohol (IV) as such is synthesized by, for example, the method described in Japanese Patent Examined Publication No. 85372/1986, or a modification thereof.

Alcohol (IV), as having a group for A represented by the following formula:

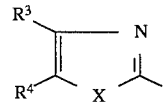

wherein the symbols have the same definitions as above, can, for example, be produced as follows:

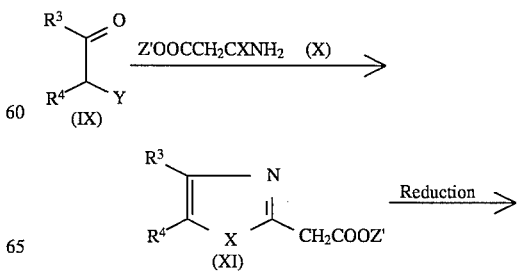

-continued

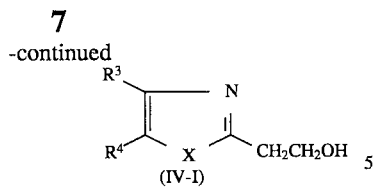

wherein Z' represents a lower alkyl group; the other symbols have the same definitions as above.

The lower alkyl group represented by Z' is exemplified by alkyl groups having 1 to 4 carbon atoms (e.g., methyl, ethyl, propyl, isopropyl, butyl, isobutyl).

In the present method, compound (IX) is reacted with malonic monoamide or malonic monothioamide derivative (X) to yield compound (XI), which is then reduced to compound (IV-1).

The reaction of (IX) and (X) is carried out in the absence of solvent or in a solvent which does not affect the reaction. Such solvents include benzene, toluene, xylene, pyridine, chloroform, carbon tetrachloride, dichloromethane, 1,2-dichloroethane, 1,1,2,2-tetrachloroethane, N,N-dimethylformamide, dimethylsulfoxide, tetrahydrofuran, dioxane, methanol, ethanol, propanol and isopropanol. Reaction temperature is normally about 20° to 200° C., preferably 50° to 150° C., reaction time being about 30 minutes to 10 hours. The amount of compound (X) used is normally about 1 to 10 mol, preferably about 1 to 5 mol per mol of compound (IX). This reaction is followed by reduction of compound (XI) to alcohol (IV-1). This reducing reaction can be carried out by a known method. Methods of reduction which can be used for this purpose include reduction with metal hydrides, reduction with metal-hydrogen complex compounds, reduction with diborane or substituted borane, and catalytic hydrogenation. In other words, this reaction is achieved by treating compound (XI) with a reducing agent. Reducing agents include alkali metal borohydrides (e.g., sodium borohydride, lithium borohydride), metal-hydrogen complex compounds such as lithium aluminum hydride, metal hydrides such as sodium hydride, organic tin compounds (e.g., triphenyltin hydride), metals and metal salts such as nickel compounds and zinc compounds, catalytic reducing agents based on a combination of a transition metal such as palladium, platinum or rhodium and hydrogen, and diborane. This reaction is carried out in an organic solvent which does not affect the reaction. Such solvents include aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, alcohols such as methanol, ethanol, propanol, isopropanol and 2-methoxyethanol, amides such as N,N-dimethylformamide, and mixtures thereof, chosen as appropriate for the reducing agent. Reaction temperature is normally about −20° to 150° C., preferably 0° to 100° C., reaction time being about 1 to 24 hours.

Compound (I-2) can be produced by reaction of compound (III) and 2,4-thiazolidinedione

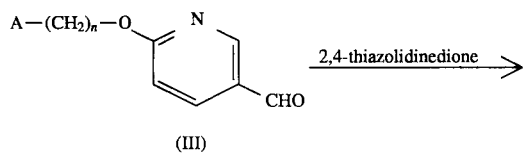

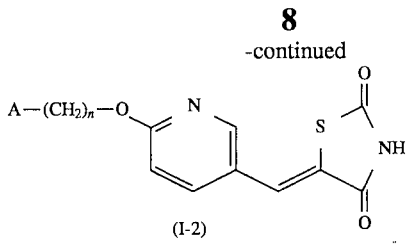

In the above formulas, the symbols have the same definitions as above.

Condensation of compound (III) and 2,4-thiazolidinedione is carried out in a solvent in the presence of a base. The solvent is exemplified by alcohols such as methanol, ethanol, propanol, isopropanol and 2-methoxyethanol, aromatic hydrocarbons such as benzene, toluene and xylene, ethers such as ethyl ether, isopropyl ether, dioxane and tetrahydrofuran, N,N-dimethylformamide, dimethyl sulfoxide and acetic acid. Said base is exemplified by sodium alkoxides (e.g., sodium methoxide, sodium ethoxide), potassium carbonate, sodium carbonate, sodium hydride, sodium acetate, and secondary amines such as piperidine, piperazine, pyrrolidine, morpholine, diethylamine and diisopropylamine. The amount of 2,4-thiazolidinedione used is 1 to 10 mol, preferably 1 to 5 mol per mol of compound (III). The amount of base used is 0.01 to 5 mol, preferably 0.05 to 2 mol per mol of compound (III). This reaction is normally carried out at 0° to 150° C., preferably 20° to 100° C., for 0.5 to 30 hours.

The 2,4-thiazolidinedione derivative (I-2) thus obtained can be isolated and purified by known means of separation and purification such as ordinary concentration, concentration under reduced pressure, solvent extraction, crystallization, recrystallization, re-dissolution and chromatography.

Compound (I-2) may be converted to compound (I-1) as follows:

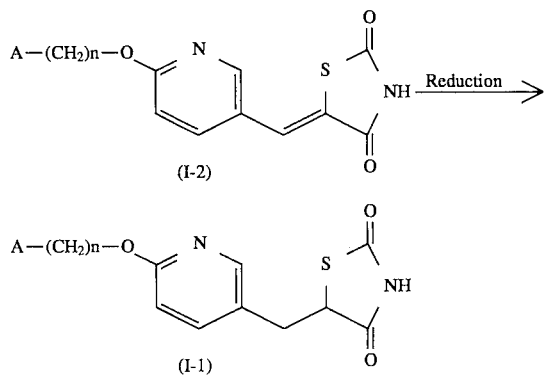

In the above formulas, the symbols have the same definitions as above.

This reducing reaction is carried out in a solvent in the presence of a catalyst in a hydrogen atmosphere of 1 to 150 atm by a conventional method. The solvent is exemplified by alcohols such as methanol, ethanol, propanol, isopropanol and 2-methoxyethanol, aromatic hydrocarbons such as benzene, toluene and xylene, ethers such as ethyl ether, isopropyl ether, dioxane and tetrahydrofuran, halogenated hydrocarbons such as chloroform, dichloromethane and 1,1,2,2-tetrachloroethane, ethyl acetate, acetic acid and mixtures thereof. The reaction is advantageously carried out when a metal catalyst such as a nickel compound catalyst or a transition metal catalyst such as palladium, platinum or rhodium is used. Reaction temperature is 0° to 100° C., preferably 10° to 80° C., reaction time being 0.5 to 50 hours.

The 2,4-thiazolidinedione derivative (I-1) thus obtained can be isolated and purified by known means of separation and purification such as ordinary concentration, concentration under reduced pressure, solvent extraction, crystallization, recrystallization, re-dissolution and chromatography.

Pyridine aldehyde derivative (III), used for the present method, can, for example, be produced as follows:

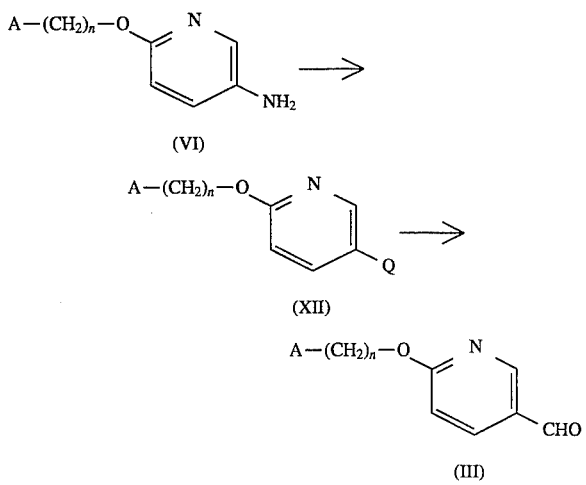

In formula (XII), Q represents chlorine, bromine or iodine; the other symbols have the same definitions as above.

In this method, compound (VI) is first subjected to a known procedure of Sandmeyer reaction to yield halogen derivative (VII). In this reaction, compound (VI) is diazotized via dropwise addition of an aqueous solution of sodium nitrite ($NaNO_2$) in a solvent in the presence of hydrochloric acid, hydrobromic acid or hydroiodic acid, followed by reaction with an aqueous solution of sodium halide or potassium halide, to yield compound (XII). Said solvent is exemplified by alcohols such as methanol, ethanol, propanol, isopropanol and 2-methoxyethanol, ethers such as acetone, 2-butanone, dioxane and tetrahydrofuran and mixtures thereof. Reaction temperature is normally −50° to 100° C., preferably −20° to 60° C., reaction time being 0.5 to 50 hours. Compound (XII) is then treated with butyl lithium, sec-butyl lithium, tert-butyl lithium, methyllithium, phenyllithium, phenylmagnesium bromide or the like, after which it is reacted with N,N-dimethylformamide (DMF) to yield compound (III). This reaction is carried out in a solvent by a conventional method. The solvent is exemplified by ethers such as ethyl ether, isopropyl ether, dioxane and tetrahydrofuran. The amount of N,N-dimethylformamide (DMF) used is 1 to 3 mol, preferably 1 to 2 mol per mol of compound (XII). Reaction temperature is −80° to 50° C., preferably −80° to 20° C., reaction time being 0.5 to 50 hours.

The pyridine aldehyde derivative (III) thus obtained can be isolated and purified by known means of separation and purification such as ordinary concentration, concentration under reduced pressure, solvent extraction, crystallization, recrystallization, re-dissolution and chromatography.

Hypoglycemic and hypolipidemic action in mice

The subject compound, at 0.01% or 0.001% in powdered food (CE-2, Clea Japan), was administered to KKA$^y$ mice (at 10 to 14 weeks of age) for 4 days. The animals had free access to water. Blood was collected from the orbital venous plexus and plasm glucose and plasma triglyceride were assayed by enzyme method using Iatrochem-GLU(A) and Iatro-MA701TG kit (Iatron). For each item, percent reduction from the control group not receiving the test compound was calculated.

| Compound (Example No.) | Dose[1] (%) | Hypoglycemic Action (%) | Hypolipidemic[2] Action (%) |
|---|---|---|---|
| 1 | 0.01 | 56 | 85 |
| 2 | 0.001 | 58 | 51 |
| 3 | 0.001 | 52 | 60 |
| 4 | 0.001 | 31 | 34 |
| 6 | 0.001 | 62 | 71 |
| 7 | 0.001 | 17 | 29 |
| 8 | 0.001 | 17 | 24 |
| 10 | 0.001 | 29 | 14 |
| 17 | 0.001 | 45 | 43 |

[1]Concentration of compound in diet
[2]Triglyceride lowering action

As stated above, thiazolidinedione compound (I) of the present invention exhibits excellent hypoglycemic and hypolipidemic action, and is pharmaceutically useful as a therapeutic agent for diabetes mellitus, hyperlipidemia and hypertension.

EXAMPLE 1

A mixture of 2-imino-5-[[2-[2-(5-methyl-2-phenyl-4-oxazolyl)ethoxy]-5-pyridyl] methyl]-4-thiazolidinone (0.76 g), 1N HCl (10 ml) and ethanol (10 ml) was heated for 20 hours while refluxing, followed by concentration under reduced pressure. The residual crystal was collected by filtration, washed with water and then recrystallized from ethanol-chloroform to yield 5-[[2-[2-( 5-methyl-2-phenyl-4-oxazolyl)ethoxy]-5-pyridyl]methyl]-2,4-thiazolidinedione (0.45 g, 59%) as a colorless crystal.

Melting point: 191.0° to 192.0° C.

Elemental analysis (for $C_{21}H_{19}N_3O_4S$): Calculated: C, 61.60; H, 4.68; N, 10.26 Found: C, 61.20; H, 4.66; N, 10.08

EXAMPLE 2

5-[[2-[2-(5-methyl-2-(2-thienyl)-4-oxazolyl)ethoxy]-5-pyridyl]methyl]- 2,4-thiazolidinedione was obtained in the same manner as in Example 1 (recrystallized from ethanol-chloroform) as a colorless crystal.

Melting point: 174° to 176° C.

EXAMPLE 3

A mixture of 2-bromo-3-[2-[2-(5-methyl-2-phenyl-4-thiazolyl)ethoxy]-5-pyridyl] propionic acid methyl ester (1.40 g), thiourea (0.25 g) and ethanol (20 ml) was heated for 4.5 hours while refluxing, followed by addition of 2N hydrochloric acid (20 ml) and heating for 18 more hours under refluxing conditions. The reaction mixture was added to water and extracted with dichloromethane. After the dichloromethane layer was washed with water and dried ($MgSO_4$), the solvent was distilled off. The residual crystal was recrystallized from ethanol-chloroform to yield 5-[[2-[2-(5-methyl-2-phenyl-4-thiazolyl)ethoxy] -5-pyridyl]methyl]-2,4-thiazolidinedione (0.66 g, 51%) as a colorless crystal.

Melting point: 195.0° to 197.0° C.

EXAMPLE 4

5-[[2-[2-[2-(2-furyl)-5-methyl-4-oxazolyl]ethoxy]-5-pyridyl]methyl] -2,4-thiazolidinedione was obtained in the same manner as in Example 3 (recrystallized from ethanol-chloroform) as a colorless crystal.

Melting point: 160.5°–162° C.

EXAMPLES 5–15

By a similar manner to Example 3, the compounds shown in Table 2 were obtained.

TABLE 2

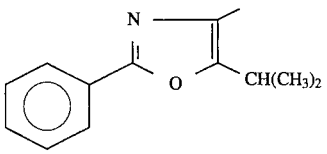

| Example No. | A | n | Yield (%) | Melting point | Recrystallization solvent |
|---|---|---|---|---|---|
| 5 | 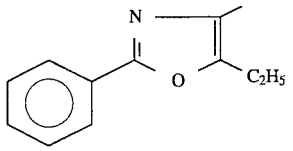 | 2 | 55 | 141–142 | ethyl acetate-ether-hexane |
| 6 | 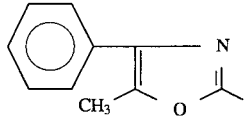 | 2 | 52 | 135–136 | ethanol-chloroform-ethyl acetate |
| 7 | 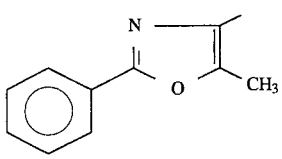 | 2 | 4 | 101–102 | ethanol-chloroform-ethyl acetate |
| 8 | 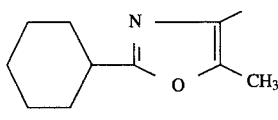 | 3 | 36 | 134–136 | ethyl acetate-hexane-isopropyl ether |
| 9 | 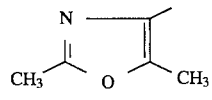 | 2 | 42 | 113–114 | ether-hexane |
| 10 | 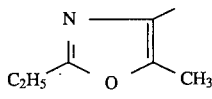 | 2 | 11 | 212–213 | ethanol-chloroform-ether |
| 11 | 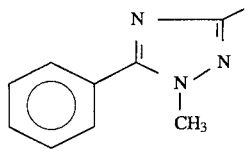 | 2 | 39 | 182–183 | methanol-dichloromethane-ether |
| 12 | 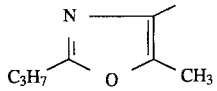 | 2 | 34 | 185–186 | methanol-chloroform-ether |
| 13 |  | 2 | 53 | 127–128 | methanol-chloroform-ether |

TABLE 2-continued

A—(CH₂)n-O—[pyridine]—CH₂—CH(S-C(=O)-CH₃)—C(=O)—NH— (structure at top)

| Example No. | A | n | Yield (%) | Melting point | Recrystallization solvent |
|---|---|---|---|---|---|
| 14 | 2-naphthyl-C(=N)-O-C(CH₃)= (oxazole) | 2 | 41 | 175–176 | methanol-chloroform-ether |
| 15 | 4-methylphenyl-C(=N)-O-C(CH₃)= (oxazole) | 2 | 59 | 178–179 | methanol-chloroform-ether |

EXAMPLE 16

5-[[2-[2-(4-benzyl-5-methyl-2-oxazolyl)ethoxy]-5-pyridyl]methyl]-2,4-thiazolidinedione, obtained in the same manner as in Example 1, was then recrystallized from ethyl acetate-hexane-isopropyl ether to yield a colorless crystal.

Melting point: 110°–111° C.

EXAMPLE 17

A mixture of 5-formyl-2-[2-(5-methyl-2-phenyl-4-oxazolyl)ethoxy]pyridine (0.6 g), 2,4-thiazolidinedione (0.235 g), piperidine (0.066 ml) and ethanol (20 ml) was heated for 9 hours while refluxing. The reaction mixture was poured into water; the separating crystal, collected by filtration, was then recrystallized from ethanol-chloroform to yield 5-[[2-[2-(5-methyl-2-phenyl-4-oxazolyl)ethoxy]-5-pyridyl]methylidene]-2,4-thiazolidinedione (0.232 g, 29%) as a yellow crystal.

Melting point: 195°–196° C.

EXAMPLE 18

A mixture of 2-(5-methyl-2-phenyl-4-oxazolylmethoxy)-5-pyridinecarboxyaldehyde (1.20 g), 2,4-thiazolidinedione (720 mg), piperidine (175 mg) and ethanol (30 ml) were heated under reflux for 10 hours. Water was added to the reaction mixture, and the separating crystals were collected by filtration and washed with ethanol to obtain 5-[[2-(5-methyl-2-phenyl-4-oxazolylmethoxy)-5-pyridyl]methylidene]-2,4-thiazolidinedione (1.35 g, 85%). Recrystallization from dichloromethane-methanol gave colorless needles.

Melting point: 225°–226° C.

Elemental analysis (for $C_{20}H_{15}N_3O_4S$) Calculated: C, 61.06; H, 3.84; N, 10.68 Found: C, 60.82; H, 3.72; N, 10.76

EXAMPLE 19

A mixture of 5-[[2-(5-methyl-2-phenyl-4-oxazolylmethoxy)-5-pyridyl]methylidene]-2,4-thiazolidinedione (1.00 g), palladium-carbon (5%, 1.00 g) and tetrahydrofuran (80 ml) was subjected to catalytic reduction at room temperature and 1 atom for 6 hours. The catalyst was filtered off, and palladium-carbon (2.00 g) was added and the mixture was further subjected to catalytic reduction at room temperature and 1 atom for 6 hours. The catalyst was filtered off. The filtrate was evaporated under reduced pressure and the residue was subjected to silica gel column chromatography. From the fraction eluted with 2% methanol-chloroform, crystals (520 mg, 52%) of 5-[[2-(5-methyl- 2-phenyl-4-oxazolylmethoxy)-5-pyridyl]methyl]-2,4-thiazolidinedione were obtained. Recrystallization from dichloromethane-isopropyl ether gave colorless prisms. Melting point: 151°–152° C.

Elemental analysis (for $C_{20}H_{17}N_3O_4$) Calculated: C, 60.75; H, 4.33; N, 10.63 Found: C, 60.52; H, 4.36; N, 10.48

EXAMPLE 20

By a similar manner to Example 3, 5-[[2-[2-[2-(2-chlorophenyl)-5-methyl- 4-oxazolyl]ethoxy]-5-pyridyl]methyl]-2,4-thiazolidinedione was obtained. Recrystallization from methanol-dichloroethanediethyl ether gave colorless crystals. Melting point: 176°–177° C.

REFERENCE EXAMPLE 1

To a solution of 2-chloro-5-nitropyridine (25 g) and 2-(5-methyl-2-phenyl- 4-oxazolyl)ethanol (32.1 g) in THF (250 ml), sodium hydride in oil (60%, 6.92 g) was added gradually while the solution was stirred under ice cooling conditions. The reaction mixture was stirred at room temperature for 15 more hours, after which it was added to water and extracted with ethyl acetate. After the ethyl acetate layer was washed with water and dried (MgSO₄), the solvent was distilled off under reduced pressure. The residual crystal was collected by filtration and recrystallized from ethanol to yield 2-[ 2-(5-methyl-2-phenyl-4-oxazolyl)ethoxy]-5-nitropyridine (25.4 g, 49%) as a yellow-brown crystal.

Melting point: 110.5° to 111.5° C.

Elemental analysis (for $C_{17}H_{15}N_3O_4$): Calculated: C, 62.76; H, 4.65; N, 12.92 Found: C, 62.80; H, 4.58; N, 12.96

REFERENCE EXAMPLE 2

2-[2-(5-methyl-2-(2-thienyl)-4-oxazolyl)ethoxy]-5-nitropyridine was obtained in the same manner as in Reference Example 1 (recrystallized from ethyl acetate-hexane) as a light yellow crystal.

Melting point: 125.5° to 126° C.

REFERENCE EXAMPLE 3

2-[2-(2-(2-furyl)-5-methyl-4-oxazolyl)ethoxy]-5-nitropyridine was obtained in the same manner as in Reference Example 1 (recrystallized from ethyl acetate-hexane) as a light yellow crystal.

Melting point: 120.0° to 121.5° C.

REFERENCE EXAMPLE 4

2-[2-(5-methyl-2-phenyl-4-thiazolyl)ethoxy]-5-nitropyridine was obtained in the same manner as in Reference Example 1 (recrystallized from ethyl acetate-hexane) as a light yellow crystal.

Melting point: 131.0° to 132.0° C.

REFERENCE EXAMPLE 5

A mixture of 2-[2-(5-methyl-2-phenyl-4-oxazolyl)ethoxy]-5-nitropyridine (13.4 g), palladium-carbon (5%, 1.5 g), ethyl acetate (200 ml), and methanol (150 ml) was catalytically reduced at room temperature at 1 atm. After the catalyst was filtered off, the filtrate was concentrated under reduced pressure, and the resulting residual crystal was collected by filtration and recrystallized from ethyl acetate-hexane to yield 5-amino-2-[2-(5-methyl-2-phenyl-4-oxazolyl)ethoxy]pyridine (11.4 g, 93%) as a brown crystal.

Melting point: 107.0° to 108.0° C.

Elemental analysis (for $C_{17}H_{17}N_3O_2$): Calculated: C, 69.14; H, 5.80; N, 14.23 Found: C, 69.01; H, 5.94; N, 13.99

REFERENCE EXAMPLE 6

5-amino-2-[2-(5-methyl-2-(2-thienyl)-4-oxazolyl)ethoxy]pyridine was obtained in the same manner as in Reference Example 5 (recrystallized from ethyl acetate-hexane) as a light brown crystal.

Melting point: 120° to 122° C.

REFERENCE EXAMPLE 7

5-amino-2-[2-[2-(2-furyl)-5-methyl-4-oxazolyl]ethoxy]pyridine was obtained in the same manner as in Reference Example 5 (recrystallized from ethyl acetate-ether-hexane) as a light brown crystal.

Melting point: 88.0° to 90.0° C.

REFERENCE EXAMPLE 8

5-amino-2-[2-(5-methyl-2-phenyl-4-thiazolyl)ethoxy]pyridine was obtained in the same manner as in Reference Example 5 (recrystallized from ethyl acetate-ether-hexane) as a light brown crystal.

Melting point: 89.0° to 91.0° C.

REFERENCE EXAMPLE 9

To a mixture of 5-amino-2-[2-(5-methyl-2-phenyl-4-oxazolyl) ethoxy]pyridine (4.5 g), aqueous HBr (47%, 7.1 ml) and acetone (70 ml) was added an aqueous solution of sodium nitrite ($NaNO_2$) (1.17 g) in water (5 ml) dropwise at a temperature of under 10° C. After stirring at 10° C. for 30 minutes, the temperature was increased to 30° C., and methyl acrylate (8.3 ml) was added. Then, cuprous oxide ($Cu_2O$) (0.1 g) was added little by little, and the mixture was vigorously stirred. The reaction mixture was further stirred at 40° to 45° C. for 1 more hour and then concentrated under reduced pressure. After alkalinization with concentrated aqueous ammonia, the residue was extracted with ethyl acetate. After the ethyl acetate layer was washed with water and dried ($MgSO_4$), the solvent was distilled off under reduced pressure. The residual oily substance was subjected to silica gel chromatography. From the fraction eluted with ethyl acetate-hexane (2:1, v/v), 2-bromo-3-[2-[2-(5-methyl-2-phenyl-4-oxazolyl]ethoxy]-5-pyridyl] propionic acid methyl ester (4.7 g, 68%) was obtained. NMR (δ ppm in $CDCl_3$): 2.34 (3H, s), 2.98 (2H, t, J=6.7 Hz), 3.16 (1H, dd, J=7.0 & 14.5 Hz), 3.37 (1H, dd, J=8.0 & 14.5 Hz), 3.74 (3H, s), 4.31 (1H, dd, J=8.0 & 7.0 Hz), 4.55 (2H, t, J=6.7 Hz), 6.67 (1H, d, J=8.6 Hz), 7.35–7.50 (4H, m), 7.90–8.05 (3H, m)

REFERENCE EXAMPLE 10

2-bromo-3-[2-[2-[5-methyl-2-(2-thienyl)-4-oxazolyl]ethoxy]-5-pyridyl] propionic acid methyl ester was obtained in the same manner as in Reference Example 9. NMR (δ ppm in $CDCl_3$): 2.31 (3H, s), 2.95 (2H, t, J= 6.7 Hz), 3.16 (1H, dd, J=7.2 & 14.4 Hz), 3.37 (1H, dd, J=8.2 & 14.4 Hz), 3.74 (3H, s), 4.32 (1H, dd, J=8.0 & 7.2 Hz), 4.52 (2H, t, J=6.8 Hz), 6.66 (1H, d, J= 8.4 Hz), 7.07 (1H, dd, J=5.0 & 3.6 Hz), 7.36 (1H, dd, J=5.0 & 1.2 Hz), 7.42(1H, dd, J=8.4 & 2.6 Hz), 7.58 (1H, dd, J=3.7 & 1.1 Hz), 7.99 (1H, d, J= 2.2 Hz)

REFERENCE EXAMPLE 11

2-bromo-3-[2-[2-[2-(2-furyl)-5-methyl-4-oxazolyl]ethoxy]-5-pyridyl] propionic acid methyl ester was obtained in the same manner as in Reference Example 9. NMR (δ ppm in $CDCl_3$): 2.32 (3H, s), 2.96 (2H, t, J= 6.7 Hz), 3.16 (1H, dd, J=7.4 & 14.4 Hz), 3.37 (1H, dd, J=8.1 & 14.6 Hz), 3.74 (3H, s), 4.32 (1H, dd, J=8.2 & 7.2 Hz), 4.54 (2H, t, J=6.7 Hz), 6.51 (1H, dd, J= 3.4 & 1.8 Hz), 6.66 (1H, d, J=8.4 Hz), 6.92 (1H, d, J=3.6 Hz), 7.43 (1H, dd, J=8.5 & 2.5 Hz), 7.52 (1H, d, J=1.8 Hz), 8.00 (1H, d, J=2.6 Hz)

REFERENCE EXAMPLE 12

2-bromo-3-[2-[2-(5-methyl-2-phenyl-4-thiazolyl)ethoxy]-5-pyridyl] propionic acid methyl ester was obtained in the same manner as in Reference Example 9. NMR (δ ppm in $CDCl_3$): 2.43 (3H, s), 3.16 (1H, dd, J= 7.1 & 14.5 Hz), 3.19 (2H, t, J=7.0 Hz), 3.37 (1H, dd, J=8.1 & 14.3 Hz), 3.74 (3H, s), 4.32 (1H, dd, J=8.1 & 7.2 Hz), 4.63 (2H, t, J=7.0 Hz), 6.67 (1H, d, J= 8.4 Hz), 7.34–7.47 (4H, m), 7.83–7.93 (2H, m), 8.01 (1H, d, J=2.6 Hz)

REFERENCE EXAMPLE 13

A mixture of 2-bromo-3-[2-[2-(5-methyl-2-phenyl-4-oxazolyl)ethoxy]-5-pyridyl] propionic acid methyl ester (1.07 g), thiourea (0.2 g), sodium acetate (0.22 g) and ethanol (25 ml) was heated for 2.5 hours while refluxing. To the reaction mixture was added a saturated aqueous solution of $NaHCO_3$ and ether, and the resulting crystal was collected by filtration, to yield 2-imino-5-[ 2-[2-(5-methyl-2-phenyl-4-oxazolyl)ethoxy]-5-pyridyl]-4-thiazolidinone (0.86 g, 88%) (recrystallized from chloroform-methanol) as a colorless crystal.

Melting point: 213° to 214° C.

Elemental analysis (for $C_{21}H_{20}N_4O_3S$): Calculated: C, 61.75; H, 4.94; N, 13.72 Found: C, 61.76; H, 5.00; N, 13.89

REFERENCE EXAMPLE 14

2-Imino-5-[2-[2-[5-methyl-2-(2-thienyl)-4-oxazolyl]ethoxy]-5-pyridyl]-4-thiazolidinone was obtained in the same manner as in Reference Example 13 (recrystallized from ethanol-chloroform) as a colorless crystal.

Melting point: 193° to 194.5° C.

REFERENCE EXAMPLE 15

By a similar manner to Reference Example 13, 5-[2-[2-(4-benzyl-5-methyl- 2-oxazolyl)ethoxy]-5-pyridyl]methyl]-2-imino-4-thiazolidinone was obtained. Recrystallization from methanol-chloroform-ether gave colorless crystals. Melting point 135°–136° C.

REFERENCE EXAMPLES 16–27

By a similar manner to Reference Example 1, compounds shown in Tables 3 and 4 were obtained.

TABLE 3

A—(CH$_2$)n-O—[pyridyl]—NO$_2$

| Reference Example No | A | n | Yield (%) | Melting point | Recrystallization solvent |
|---|---|---|---|---|---|
| 16 | phenyl-C(=N)-O-C(=)-CH(CH$_3$)$_2$ oxazole | 2 | 53 | 91–92 | ethyl acetate-hexane |
| 17 | phenyl-C(=N)-O-C(=)-C$_2$H$_5$ oxazole | 2 | 64 | 100–101 | ethyl acetate hexane |
| 18 | phenyl-C(CH$_3$)=C-N=C(CH$_3$)-O oxazole | 2 | 70 | 119–120 | ethyl acetate-hexane |
| 19 | phenyl-C(=N)-O-C(=)-CH$_3$ oxazole | 3 | 58 | 103–104 | ethyl acetate-hexane-isopropyl ether |
| 20 | cyclohexyl-C(=N)-O-C(=)-CH$_3$ oxazole | 2 | 86 | 70–71 | ethyl acetate hexane |
| 21 | CH$_3$-C(=N)-O-C(=)-CH$_3$ oxazole | 2 | 82 | 83–84 | ether-hexane |
| 22 | C$_2$H$_5$-C(=N)-O-C(=)-CH$_3$ oxazole | 2 | 55 | 85–86 | ether-hexane |

TABLE 3-continued

A—(CH₂)n-O—[pyridine with NO₂]

| Reference Example No | A | n | Yield (%) | Melting point | Recrystallization solvent |
|---|---|---|---|---|---|
| 23 | 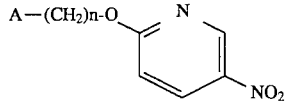 | 2 | 71 | 152–153 | ethyl acetate-ether |

TABLE 4

| Reference Example No | A | n | Yield (%) | Melting point | Recrystallization solvent |
|---|---|---|---|---|---|
| 24 | 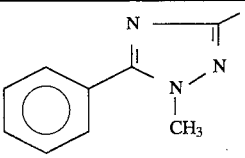 | 2 | 65 | 63–64 | ether-hexane |
| 25 | 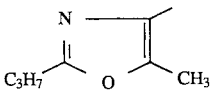 | 2 | 59 | 122–123 | ethyl acetate-isopropyl ether |
| 26 | 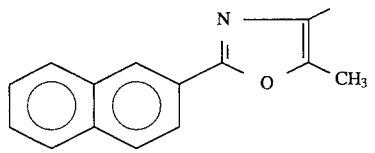 | 2 | 80 | 127–128 | ethyl acetate-hexane |
| 27 | 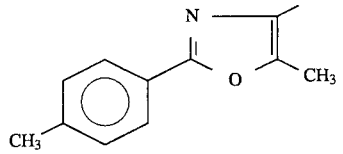 | 2 | 83 | oil[1] | |

[1] Purified by column chromatography on silica gel.
NMR (δ ppm) in CDCl₃: 2.20(3H, s), 3.20(2H, t, J=6.7Hz), 3.77(2H, s), 4.79(2H, t, J=6.8Hz), 6.80(1H, d, J=9.2Hz), 7.10–7.37(5H, m), 8.33(1H, dd, J=2.8&9.2Hz), 9.04(1H, d, J=3.0Hz).

REFERENCE EXAMPLES 28–39

By a similar manner to Reference Example 5, compounds shown in Tables 5 and 6 were obtained.

TABLE 5

A—(CH₂)n—O—[pyridine]—NH₂

| Reference Example No | A | n | Yield (%) | Melting point | Recrystallization solvent |
|---|---|---|---|---|---|
| 28 | Ph−C(=N−)−O−C(CH₃)=CH−CH(CH₃)₂ | 2 | 93 | 125–126 | ethyl acetate-isopropyl ether-hexane |
| 29 | Ph−C(=N−)−O−C(CH₃)=CH−C₂H₅ | 2 | 91 | 114–115 | ethyl acetate-isopropyl ether hexane |
| 30 | Ph−C(CH₃)=C(CH₃)−N=C(CH₃)−O− (structure) | 2 | quant. | oil[1] | |
| 31 | Ph−C(=N−)−O−C(CH₃)=CH−CH₃ | 3 | 92 | oil[2] | |
| 32 | Cy−C(=N−)−O−C(CH₃)=CH−CH₃ | 2 | 95 | oil[3] | |
| 33 | CH₃−C(=N−)−O−C(CH₃)=CH−CH₃ | 2 | 99 | oil[4] | |
| 34 | C₂H₅−C(=N−)−O−C(CH₃)=CH−CH₃ | 2 | quant. | oil[5] | |
| 35 | Ph−C(=N−)−N(CH₃)−N=C(CH₃)− (pyrazole) | 2 | 98 | 160–161 | methanol-isopropyl ether |

[1] NMR(δ ppm in CDCl₃): 2.50(3H, s), 3.23(2H, t, J=6.8Hz), 4.62(2H, t, J=6.9Hz), 6.60(1H, d, J=8.8Hz), 7.02(1H, dd, J=2.8&8.6Hz), 7.22–7.46(3H, m)7.58–7.68(3H, m).
[2] NMR(δ ppm in CDCl₃): 2.03–2.23(2H, m), 2.82(3H, s), 2.67(2H, t, J=7.4Hz), 4.21(2H, t, J=6.3Hz), 6.60(1H, d, J=8.8Hz), 7.03(1H, dd, J=3.0&8.6Hz), 7.37–7.49(3H, m), 7.64(1H, d, J=3.0Hz), 7.92–8.03(2H, m).
[3] NMR(δ ppm in CDCl₃): 1.17–1.93(8H, m), 1.93–2.13(2H, m), 2.20(3H, s), 2.59–2.77(1H, m), 2.85(2H, t, J=6.9Hz), 4.38(2H, t, J=6.9Hz), 6.57(1H, d, J=8.6Hz), 7.03(1H, dd, J=3.0&8.6Hz), 7.64(1H, d, J=3.0Hz).
[4] NMR(δ ppm in CDCl₃): 2.20(3H, s), 2.37(3H, s), 2.83(2H, t, J=6.8Hz), 4.39(2H, t, J=6.8Hz), 6.56(1H, d, J=8.8Hz), 7.02(1H, dd, J=2.8&8.8Hz), 7.64(1H, d, J=2.8Hz).
[5] NMR(δ ppm in CDCl₃): 1.29(3H, t, J=7.6Hz), 2.20(3H, s), 2.69(2H, q, J=7.6Hz), 2.84(2H, t, J=6.9Hz), 4.39(2H, t, J=6.9Hz), 6.55(1H, d, J=8.6Hz), 7.01(1H, dd, J=3.0&8.6Hz), 7.63(1H, d, J=3.0Hz).

TABLE 6

A—(CH₂)n-O-[pyridine]-NH₂

| Reference Example No | A | n | Yield (%) | Melting point | Recrystallization solvent |
|---|---|---|---|---|---|
| 36 | [structure with C₃H₇, N, O, CH₃] | 2 | 99 | oil[6] | |
| 37 | [naphthalene-oxazoline structure with CH₃] | 2 | 85 | 131–132 | ethyl acetate-isopropyl ether |
| 38 | [4-methylphenyl-oxazoline structure with CH₃] | 2 | 89 | 137–138 | ethyl acetate-hexane-isopropyl ether |
| 39 | [benzyl-CH₃-oxazoline structure] | 2 | 98 | oil[7] | |

[6] NMR(δ ppm in CDCl₃): 0.97(3H, t, J=7.3Hz), 1.64–1.85(2H, m), 2.20(3H, s), 2.64(2H, t, J=7.5Hz), 2.84(2H, t, J=7.0Hz), 4.39(2H, t, J=6.9Hz), 6.56(1H, d, J=8.8Hz), 7.02(1H, dd, J=3.0&8.8Hz), 7.64(1H, d, J=3.0Hz).

[7] NMR(δ ppm in CDCl₃): 2.18(3H, s), 3.14(2H, t, J=6.9Hz), 3.77(2H, s), 4.55(2H, t, J=6.9Hz), 6.57(1H, d, J=8.4Hz), 7.00(1H, dd, J=3.0&8.6Hz), 7.14–7.33(5H, m), 7.62(1H, d, J=3.0Hz).

REFERENCE EXAMPLES 40–51

By a similar manner to Reference Example 9, compounds shown in Tables 7, 8 and 9 were obtained in oily substance.

TABLE 7

A—(CH₂)n-O-[pyridine]-CH₂CH(Br)COOCH₃

| Reference Example No. | A | n | Yield (%) | NMR (δ ppm in CDCl₃) |
|---|---|---|---|---|
| 40 | [phenyl-oxazoline-CH(CH₃)₂ structure] | 2 | 53 | 1.32(6H, d, J=7Hz), 2.96–3.21 (4H, m), 3.37(1H, dd, J=8.1 & 14.3Hz), 4.31(1H, dd, J=8.1 & 7.0Hz), 4.55(2H, t, J=6.7Hz), 6.66(1H, d, J=8.4Hz), 7.37–7.49(4H, m), 7.95–8.40(3H, m). |
| 41 | [phenyl-oxazoline-C₂H₅ structure] | 2 | 56 | 1.27(3H, t, J=7.5Hz), 2.70(2H, q, J=7.5Hz), 2.98(2H, t, J=6.8 Hz), 3.16(1H, dd, J=7.2 & 14.4Hz), 3.37(1H, dd, J=8.2 & 14.4 Hz), 3.74(3H, s), 4.31(1H, dd, J=8.2 & 7.2Hz), 4.54(2H, t, J=6.7Hz), 6.66(1H, d, J=8.6Hz), 7.36–7.48(4H, m), 7.92–8.02(3H, m). |

TABLE 7-continued $$A-(CH_2)_n-O-\text{[pyridine]}-CH_2CHCOOCH_3 \text{ (with Br)}$$

| Reference Example No. | A | n | Yield (%) | NMR (δ ppm in CDCl₃) |
|---|---|---|---|---|
| 42 | Ph-C(=N-O-)-C(CH₃)= (phenyl isoxazoline-type) | 2 | 53 | 2.50(3H, s), 3.10–3.45(4H, m), 3.75(3H, s), 4.32(1H, dd, J=8.0 & 7.2Hz), 4.70(2H, t, J=6.8Hz), 6.70(1H, d, J=8.4 Hz), 7.23–7.48(4H, m), 7.59–7.68(2H, m), 8.00(1H, d, J=2.6Hz) |
| 43 | Ph-C(=N-)-O-C(CH₃)= | 3 | 36 | 2.05–2.25(2H, m), 2.29(3H, s), 2.67(2H, q, J=7.3Hz), 3.16(1H, dd, J=7.2 & 14.4Hz), 3.38(1H, dd, J=8.0 & 14.4Hz), 3.75(3H, s), 4.24–4.38(3H, m), 6.70(1H, d, J=8.4Hz), 7.36–7.49(4H, m), 7.92–8.04(3H, m). |

TABLE 8

| Reference Example No. | A | n | Yield (%) | NMR (δ ppm in CDCl₃) |
|---|---|---|---|---|
| 44 | Cyclohexyl-C(=N-)-O-C(CH₃)= | 2 | 44 | 1.21–2.18(10H, m), 2.21(3H, s), 2.60–2.78(1H, m), 2.87(2H, t, J=6.9Hz), 3.16(1H, dd, J=7.2 & 14.4Hz), 3.37(1H, dd, J=8.1 & 14.3 Hz), 3.74(3H, s), 4.32(1H, dd, 8.0 & 7.2Hz), 4.45(2H, t, J=6.9 Hz), 6.66(1H, d, J=8.4Hz), 7.42(1H, dd, J=2.5 & 8.5Hz), 7.98 (1H, dd, J=2.4Hz). |
| 45 | CH₃-C(=N-)-O-C(CH₃)= (CH₃ on C=N) | 2 | 34 | 2.20(3H, s), 2.37(3H, s), 2.85(2H, t, J=6.8Hz), 3.16(1H, dd, J=7.1 & 14.3Hz), 3.37(1H, dd, J=8.0 & 14.4Hz), 3.75(3H, s), 4.32 (1H, dd, J=7.2 & 8.2Hz), 4.47(2H, t, J=6.8Hz), 6.65(1H, d, J=8.6 Hz), 7.42(1H, dd, J=2.6 & 8.4Hz), 7.99(1H, d, J=2.4Hz) |
| 46 | C₂H₅-C(=N-)-O-C(CH₃)= | 2 | 51 | 1.29(3H, t, J=7.7Hz), 2.21(3H, s), 2.70(2H, q, J=7.6Hz), 2.87 (2H, t, J=6.9Hz), 3.16(1H, dd, J=7.1 & 14.3Hz), 3.37(1H, dd, J=8.1 & 14.3Hz), 3.75(3H, s), 4.32(1H, dd, J=7.2 & 8.1Hz), 4.46(2H, t, J=6.8Hz), 6.66(1H, d, J=8.4Hz), 7.42(1H, dd, J=2.5 & 8.5H z), 7.99(1H, d, J=2.6Hz). |
| 47 | Ph-C(=N-)-N(CH₃)-N=C(CH₃) (pyrazole-type) | 2 | 45 | 3.10–3.46(4H, m), 3.74(3H, s), 3.92(3H, s), 4.32(1H, t, J=7.5H z), 4.70(2H, t, J=6.6Hz), 6.67(1H, d, J=8.4Hz), 7.30–7.50(4H, m), 7.97–8.12(3H, m). |

TABLE 9

| Reference Example No. | A | n | Yield (%) | NMR (δ ppm in CDCl₃) |
|---|---|---|---|---|
| 48 | C₃H₇-C(=N-)-O-C(CH₃)= | 2 | 32 | 0.97(3H, t, J=7.3Hz), 1.64–1.85(2H, m), 2.21(3H, s), 2.64 (2H, t, J=7.5Hz), 2.87(2H, t, J=6.9Hz), 3.16(1H, dd, J=7.2 & 14.4Hz), 3.37(1H, dd, J=8.1 & 14.5Hz), 3.75(3H, s), 4.32(1H, dd, J=7.2 & 8.2Hz), 4.46(2H, t, J=6.8Hz), 6.66(1H, d, J= 8.4Hz), 7.42(1H, dd, J=2.6 & 8.4Hz), 7.99(1H, d, J=2.6Hz). |

TABLE 9-continued

| Reference Example No. | A | n | Yield (%) | NMR (δ ppm in CDCl$_3$) |
|---|---|---|---|---|
| 49 | naphthalen-2-yl-C(=N)-O-C(CH$_3$)= | 2 | 28 | 2.38(3H, s), 3.02(2H, t, J=6.0Hz), 3.16(1H, dd, J=7.2 & 14.4Hz), 3.37(1H, dd, J=8.0 & 14.2Hz), 3.74(3H, s), 4.32(1H, dd, J=7.1 & 8.1Hz), 4.58(2H, t, J=6.8Hz), 6.68(1H, d, J= 8.4Hz), 7.38–7.57(3H, m), 7.79–7.96(3H, m), 8.08(1H, dd, J= 1.7 & 8.7Hz), 8.10(1H, d, J=2.6Hz), 8.47(1H, s) |
| 50 | 4-methylphenyl-C(=N)-O-C(CH$_3$)= | 2 | 36 | 2.32(3H, s), 2.38(3H, s), 2.97(2H, t, J=6.8Hz), 3.16(1H, dd, J= 7.2 & 14.4Hz), 3.37(1H, dd, J=8.0 & 14.4Hz), 3.74(3H, s), 4.32 (1H, dd, J=7.3 & 8.2Hz), 4.54(2H, t, J=6.8Hz), 6.67(1H, d, J=8.4Hz), 7.23(1H, d, J=8.0Hz), 7.43(1H, dd, J=2.6 & 8.4 Hz), 7.87(2H, d, J=8.2Hz), 8.00(1H, d, J=2.6Hz). |
| 51 | phenyl-CH$_2$-C(CH$_3$)=C(O-)-N- (isopropyl) | 2 | 45 | 2.18(3H, s), 3.08–3.23(3H, m), 3.37(1H, dd, J=8.1 & 14.5Hz), 3.75(3H, s), 3.77(2H, s), 4.32(1H, dd, J=8.0 & 7.2Hz), 4.63(2H, t, J=6.9Hz), 6.67(1H, d, J=8.4Hz), 7.13–7.34(5H, m), 7.42 (1H, dd, J=2.5 & 8.5Hz), 7.98(1H, d, J=2.2Hz) |

REFERENCE EXAMPLE 52

To a mixture of 5-amino-2-[2-(5-methyl-2-phenyl-4-oxazolyl) ethoxy]pyridine (10.0 g), conc. HCl (8.47 ml) and acetone (100 ml), a solution of sodium nitrite (NaNO$_2$) (2.46 g) in water (10 ml) was added dropwise at a temperature of under 10° C. After mixture was stirred at 10° C. for 30 minutes, a solution of potassium iodide (KI) (2.46 g) in water (10 ml) was added dropwise to the mixture. The reaction mixture was stirred at 30° to 35° C. for 1 hour and then at 35° to 40° C. for 1 hour, after which it was concentrated under reduced pressure. The residue was poured into water and extracted with ethyl acetate. After the ethyl acetate layer was washed with water and dried (MgSO$_4$), the solvent was distilled off under reduced pressure. The residual oily substance was subjected to silica gel chromatography. From the fraction eluted with ethyl acetate-hexane (1:3, v/v), 5-iodo-2-[2-(5-methyl-2-phenyl-4-oxazolyl)ethoxy] pyridine (7.22 g, 52%) was obtained, which was then recrystallized from ethyl acetate-hexane to yield a colorless crystal.

Melting point: 105°–106° C.

REFERENCE EXAMPLE 53

To a solution of 5-iodo-2-[2-(5-methyl-2-phenyl-4-oxazolyl) ethoxy]pyridine (2.5 g) in tetrahydrofuran (40 ml), a solution of n-butyl lithium in hexane (1.6M, 4.61 ml) was added dropwise at −65° C. in a nitrogen stream. After the mixture was stirred at the same temperature for 15 minutes, N,N-dimethylformamide (0.71 ml) was added dropwise. After the cooling bath was removed and the mixture was stirred for 30 more minutes, a saturated aqueous solution of ammonium chloride (6 ml) was added. The reaction mixture was poured into water and extracted with ethyl acetate. After the ethyl acetate layer was washed with water and dried (MgSO$_4$), the solvent was distilled off under reduced pressure, to yield 5-formyl-2-[2-(5 -methyl-2-phenyl-4-oxazolyl)ethoxy]pyridine (1.5 g, 79%), which was then recrystallized from ethyl acetate-hexane to yield a colorless crystal.

Melting point: 99°–100° C.

REFERENCE EXAMPLE 54

A mixture of N-carbobenzoxyphenylalanine (40 g), acetic anhydride (54.7 g) and 4-(N,N-dimethylamino)pyridine (DMAP) (1.0 g) was stirred at 80° C. for 2 hours. The reaction mixture was poured into water, stirred for 2 hours and then extracted with ethyl acetate. After the ethyl acetate layer was washed successively with 2N HCl, water, a saturated aqueous solution of sodium hydrogen carbonate and water and then dried (MgSO$_4$), the solvent was distilled off under reduced pressure, to yield 3-acetylamino-4-phenyl-2-butanone (13.5 g, 49%), which was then recrystallized from ethyl acetate-isopropyl ether to yield a colorless crystal.

Melting point: 96°–97° C.

REFERENCE EXAMPLE 55

A mixture of 3-acetylamino-4-phenyl-2-butanone (12.5 g), 6N HCl (50 ml) and ethanol (50 ml) was stirred under refluxing conditions for 18 hours. The reaction mixture was concentrated under reduced pressure to yield 3-amino-4-phenyl-2-butanone hydrochloride (9.8 g, 81%).

REFERENCE EXAMPLE 56

A mixture of 3-amino-4-phenyl-2-butanone hydrochloride (9.56 g), ethyl malonyl chloride (7.72 g) and benzene (40 ml) was stirred under refluxing conditions for 4 hours. The reaction mixture was concentrated under reduced pressure; the residue was then neutralized with a saturated aqueous solution of sodium carbonate and extracted with ethyl acetate. After the ethyl acetate layer was washed with water and dried (MgSO$_4$), the solvent was distilled off under reduced pressure, to yield N-(1-benzyl-2-oxopropyl)malonamidic acid ethyl ester (7.45 g, 56%), which was then recrystallized from ethyl acetate-isopropyl ether to yield a colorless crystal.

Melting point: 68°–69° C.

REFERENCE EXAMPLE 57

A mixture of N-(1-benzyl-2-oxopropyl)malonamidic acid ethyl ester (7.0 g), phosphorus oxychloride (POCl$_3$) (5.8 g) and toluene (40 ml) was stirred under refluxing conditions for 1 hour. The reaction mixture was concentrated under reduced pressure; the residue was then neutralized with a saturated aqueous solution of sodium hydrogen carbonate and extracted with ethyl acetate. After the ethyl acetate layer was washed with water and dried (MgSO$_4$), the solvent was distilled off under reduced pressure and the residue was subjected to silica gel chromatography. From the fraction eluted with hexane-ethyl acetate (1:3, v/v), ethyl 2-(4-benzyl-5-methyl-2-oxazolyl)acetate (4.76 g, 63%) was obtained as an oily substance.

NMR (δ ppm in CDCl$_3$): 1.26 (3H, t, J=7.1 Hz), 2.21 (3H, s), 3.75 (2H, s), 3.79 (2H, s), 4.19 (2H, q, J=7.1 Hz), 7.13–7.34 (5H, m)

REFERENCE EXAMPLE 58

To a suspension of lithium aluminum hydride (LiAlH$_4$) (0.7 g) in ethyl ether (40 ml), a solution of ethyl 2-(4-benzyl-5-methyl-2-oxazolyl)acetate (4.76 g) in ethyl ether (60 ml) was added dropwise under ice cooling conditions, followed by stirring for 1 hour. After water (5 ml) was added dropwise to the reaction mixture, the insoluble substances were filtered off, and the filtrate was concentrated under reduced pressure. The residue was subjected to silica gel chromatography. From the fraction eluted with chloroform-ethyl acetate (2:1, v/v), 2-(4-benzyl-5-methyl-2-oxazolyl)ethanol (3.0 g, 75%) was obtained as an oily substance.

NMR (δ ppm in CDCl$_3$): 3.19 (3H, s), 2.88 (2H, t, J=5.7 Hz), 3.75 (2H, s), 3.94 (2H, t, J=5.8 Hz), 7.13–7.36 (5H, m)

REFERENCE EXAMPLE 59

Methylhydrazine (3.5 g) was added gradually to an ice-cooled solution of methyl benzimidate hydrochloride [C$_6$H$_5$C(=NH)OCH$_3$.HCl](13.0 g) in methanol (80 ml), followed by stirring at the same temperature for 3 hours. The separating crystal was collected by filtration to yield 2-methyl-3-phenylamidorazone hydrochloride (10.9 g), which was then recrystallized from methanol-ether.

Melting point: 197°–198° C.

REFERENCE EXAMPLE 60

A mixture of 2-methyl-3-phenylamidorazone hydrochloride (6.0 g), ethyl malonyl chloride (5.1 g) and benzene (40 ml) was stirred under refluxing conditions for 6 hours. The reaction mixture was concentrated under reduced pressure, and acetic acid (30 ml) added to the residue, followed by stirring under refluxing conditions for 3 hours. The reaction mixture was concentrated under reduced pressure; the residue was then neutralized with a saturated aqueous solution of sodium hydrogen carbonate and extracted with ethyl acetate. After the ethyl acetate layer was washed with water and dried (MgSO$_4$), the solvent was distilled off under reduced pressure and the residue was subjected to silica gel chromatography. From the fraction eluted with chloroform-ethyl acetate (4:1, v/v), 1-methyl-5-phenyl-1H-1,2,4-triazol-3-ylacetic acid ethyl ester (6.2 g, 78%) was obtained, which was then recrystallized from ether-isopropyl ether to yield colorless prisms.

Melting point: 82°–83° C.

REFERENCE EXAMPLE 61

To a mixture of aspartic acid β-methyl ester (20.0 g), sodium hydrogen carbonate (24.0 g), ethyl ether (50 ml) and water (200 ml), 2-naphthoyl chloride (25.9 g) was added dropwise under ice cooling conditions. After the mixture was stirred at room temperature for 3 hours, the organic layer was separated. The water layer was acidified with 2N HCl and then extracted with ethyl acetate. After the ethyl acetate layer was washed with water and dried (MgSO$_4$), the solvent was distilled off under reduced pressure to yield an oily substance.

The oily substance was added to a mixture of acetic anhydride (69.5 g), 4-(N,N-dimethylamino)pyridine (DMAP) (0.5 g) and pyridine (64 ml), followed by stirring at 90° C. for 1 hour. The reaction mixture was poured into water and stirred for 2 hours, after which it was extracted with ethyl acetate. After the ethyl acetate layer was washed successively with a saturated aqueous solution of sodium hydrogen carbonate, a dilute aqueous solution of phosphoric acid and water, and then dried (MgSO$_4$), the solvent was distilled off under reduced pressure to yield an oily substance.

The oily substance was dissolved in acetic anhydride (40 ml), and concentrate H$_2$SO$_4$ (4.0 ml) was added dropwise at room temperature. This mixture was stirred at 90° C. for 1 hour and then concentrated under reduced pressure. The residue was poured into water, neutralized with a saturated aqueous solution of sodium hydrogen carbonate and then extracted with ethyl acetate. After the ethyl acetate layer was washed with water and dried (MgSO$_4$), the solvent was distilled off under reduced pressure to yield 5-methyl-2-(2-naphthyl)-4-oxazoleacetic acid methyl ester (31 g, 81%), which was then recrystallized from dichloromethane-isopropyl ether to yield colorless prisms.

Melting point: 86°–87° C.

REFERENCE EXAMPLE 62

5-methyl-2-(4-methylphenyl)-4-oxazoleacetic acid methyl ester, obtained in the same manner as in Reference Example 61, was then recrystallized from ethyl acetate-hexane to yield a colorless crystal.

Melting point: 59°–60° C.

REFERENCE EXAMPLE 63

5-Isopropyl-2-phenyl-4-oxazoleacetic acid methyl ester was obtained in the same manner as in Reference Example 61.

NMR (δ ppm in CDCl$_3$): 1.33 (6H, d, J=7 Hz), 3.0–3.2(1H,m), 3.61 (2H, s), 3.73 (3H, s), 7.35–7.50 (3H, m), 7.95–8.05 (2H, m)

REFERENCE EXAMPLES 64–66

By a similar manner to Reference Example 58, compounds shown in Table 10 were obtained.

TABLE 10

A—CH₂CH₂OH

| Reference Example No | A | Yield (%) | Melting point | Recrystallization solvent |
|---|---|---|---|---|
| 64 | phenyl-C(=N—)—C(=CH—N(CH₃)—N) | 52 | 110–111 | acetone-isopropyl ether |
| 65 | naphthyl-C(=N—)—C(=CH—O)—CH₃ | 86 | 89–90 | ether-isopropyl ether |
| 66 | (4-methylphenyl)-C(=N—)—C(=CH—O)—CH₃ | 88 | 58–59 | isopropyl ether-hexane |
| 67 | phenyl-C(=N—)—C(=CH—O)—CH(CH₃)₂ | 87 | 47–48 | hexane |

REFERENCE EXAMPLE 68

By a similar manner to Reference Example 1, 2-(5-methyl-2-phenyl-4-oxazolylmethoxy)-5-nitropyridine was obtained. Recrystallization from dichloromethane-isopropyl ether gave colorless prisms. Melting point: 142°–143° C.

REFERENCE EXAMPLE 69

By a similar manner to Reference Example 5, 5-amino-2-(5-methyl-2-phenyl-4-oxazolylmethoxy)pyridine was obtained. Recrystallization from methanol-isopropyl ether gave colorless prisms. Melting point: 106°–107° C.

REFERENCE EXAMPLE 70

To a solution of 5-amino-2-(5-methyl-2-phenyl-4-oxazolylmethoxy)pyridine (7.10 g) in acetone (200 ml)-water (50 ml) was added dropwise concentrated hydrochloric acid (7.46 g) under ice cooling, and then solution of sodium nitrite (1.83 ) in water (10 ml) was added dropwise. The mixture was stirred for 10 minutes. To the mixture was added a solution of sodium iodide (4.40 g) in water (20 ml) under ice cooling. The mixture was stirred at 15°–20° C. for 2 hours. To the reaction mixture was added water, and the mixture was neutralized with a solution of sodium hydrogen carbonate. The mixture was subjected to extraction with ethyl acetate. The ethyl acetate layer was washed with water, dried over magnesium sulfate. The solvent was distilled off under reduced pressure and the residue was subjected to silica gel chromatography. From the fraction eluted with ethyl acetate-hexane (1:9, v/v), crystals (6.65 g, 67%) of 5-iodo-2-(5-methyl-2-phenyl-4-oxazolylmethoxy)pyridine were obtained. Recrystallization from ethyl acetate-hexane gave colorless prisms. Melting point: 129°–130° C.

Elemental analysis (for $C_{16}H_{13}IN_2O_2$) Calculated: C, 49.00; H, 3.34; N, 7.14 Found: C, 48.87; H, 3.10; N, 7.22

REFERENCE EXAMPLE 71

To a solution of 5-iodo-2-(5-methyl-2-phenyl-4-oxazolylmethoxypyridine (6.53 ) in tetrahydrofuran (60 ml) was added dropwise a 1.6M solution of n. butyllithium in hexane (1.6M, 10.9 ml) at −65° C., and the mixture was stirred for 20 minutes. N,N-dimethylformamide (2.43 g) was added and temperature of the reaction mixture was elevated to room temperature. An aqueous solution of ammonium chloride was added to the mixture. The mixture was subjected to extraction with ethyl acetate. The ethyl acetate layer was washed with water and dried over magnesium sulfate. The solvent was distilled off under reduced pressure and the residue was subjected to silica gel chromatography. From the fraction eluted with ethyl acetate-hexane (1:3, v/v), crystals (2.80 g, 57%) of 2-(5-methyl-2-phenyl-4 -oxazolylmethoxy)-5-pyridine carboxyaldehyde were obtained. Recrystallization from ethyl acetate-hexane gave colorless prisms. Melting point: 116°–117° C.

Elemental analysis (for $C_{17}H_{14}N_2O_3$) Calculated: C, 69.38; H, 4.79; N, 9.52 Found: C, 69.47; H, 4.75; N, 9.60

REFERENCE EXAMPLE 72

By a similar manner to Reference Example 1, 2-[2-[5-methyl-2-(2 -chlorophenyl)-4-oxazolyl]ethoxy]-5-nitropyridine was obtained. Recrystallization from ethyl acetate-ethyl ether gave pale yellow crystals. Melting point: 100°–101° C.

REFERENCE EXAMPLE 73

A mixture of 2-[2-[5-methyl-2-(2-chlorophenyl)-4-oxazolyl]ethoxy]-5-nitropyridine (1.69 g), iron dust (787 mg), acetic acid (25 ml) and water (8 ml) was stirred at 65°–70°

C. for 3 hours. Insolubles were filtered off and the filtrate was evaporated under reduced pressure. To the residue was added water. The mixture was subjected to extraction with ethyl acetate. The ethyl acetate layer was washed with water and dried over magnesium sulfate. The solvent was distilled off, and the residue was subjected to silica gel chromatography. From the fraction eluted with methanol-chloroform (1:25, v/v), 5-amino-2-[2-[ 5-methyl-2-(2-chlorophenyl)-4-oxazolyl]ethoxy]pyridine (1.50 g, 97%) was obtained.

NMR (δ ppm in CDCl$_3$): 2.36(3H,s), 2.99(2H,t,J=6.7 Hz), 4.48(2H,t,J=6.7 Hz), 6.59(1H,d,J=8.6 Hz), 7.03(1H,dd,J=3.0&9.0 Hz), 7.26–7.53(3H,m), 7.66(1H,d,J=3.0 Hz), 7.88–8.03(2H,m)

REFERENCE EXAMPLE 74

By a similar manner to Reference Example 9, 2-bromo-3-[2-[2-[2-(2 -chlorophenyl)-5-methyl-4-oxazolyl]ethoxy]-5-pyridyl]propionic acid methyl ester was obtained.

NMR (δ ppm in CDCl$_3$): 2.35(3H,s), 3.01(2H,t,J=6.6 Hz), 3.16(1H,dd,J=7.3&14.5 Hz), 3.37(1H,dd,J=8.1&14.5 Hz), 3.74(3H,s), 4.33(1H,dd,J=7.3&8.1 Hz), 4.56(2H,t,J=6.6 Hz), 6.67(1H,d,J=8.4 Hz), 7.26–7.51(4H,m), 7.87–8.03(2H,m)

PREPARATION EXAMPLE 1

Tablet production

| | |
|---|---|
| (1) Compound obtained in Example 1 | 30 mg |
| (2) Lactose | 133.4 mg |
| (3) Corn starch | 30 mg |
| (4) Hydroxypropyl cellulose | 6 mg |
| (5) Water | (0.03 ml) |
| (6) Magnesium stearate | 0.6 mg |
| | Total 200 mg |

Above components (1), (2), (3) and (4) were mixed and then kneaded with water, followed by vacuum drying at 40° C. for 16 hours. The dry product was milled in a mortar and sieved through a 16-mesh sieve to yield granules. After component (6) was added, these granules were tableted, using a rotary tableting machine (produced by Kikusui Seisakusho), to yield 200 mg tablets.

We claim:

1. A thiazolidinedione compound of the formula:

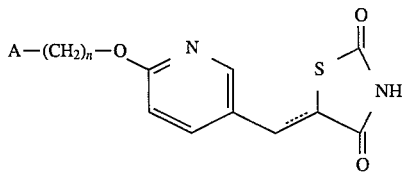

wherein n is an integer of from 1 to 3,

A is 1,2,3-triazol-4-yl or 1,2,4-triazol-3-yl, each of which may have 1 or more substituents, at any position on the ring thereof, selected from the group consisting of
  (1) an aliphatic hydrocarbon selected from the group consisting of alkyl of 1 to 8 carbon atoms, alkenyl having 2 to 8 carbon atoms and alkynyl having 2 to 8 carbon atoms,
  (2) an alicyclic hydrocarbon selected from the group consisting of cycloalkyl having 3 to 7 carbon atoms and cycloalkenyl having 5 to 7 carbon atoms,
  (3) an alicyclic-aliphatic hydrocarbon selected from the group consisting of cycloalkyl-alkyl of 4 to 9 carbon atoms, cycloalkyl-alkenyl of up to 9 carbon atoms, cycloalkyl-alkynyl of up to 9 carbon atoms, cycloalkenyl-alkyl of 4 to 9 carbon atoms, cycloalkenyl-alkenyl of up to 9 carbon atoms and cycloalkenyl-alkynyl of up to 9 carbon atoms,
  (4) phenylalkyl having 7 to 9 carbon atoms,
  (5) naphthylalkyl having 11 to 13 carbon atoms,
  (6) phenyl,
  (7) naphthyl,
  (8) thienyl,
  (9) furyl,
  (10) pyridyl,
  (11) thiazolyl,
  (12) oxazolyl,
  (13) piperidinyl,
  (14) pyrrolidinyl,
  (15) morpholinyl, and
  (16) tetrahydrofuryl, and
  each of the above substituents (2), (3), (13), (14), (15) and (16) may be substituted by 1 to 3 lower alkyl groups having 1 to 3 carbon atoms, and each of the above substituents (4), (5), (6), (7), (8), (9), (10), (11) and (12) may be substituted by 1 to 4 substituents selected from the group consisting of halogen, hydroxy, cyano, trifluoromethyl, lower alkoxy having 1 to 4 carbon atoms, lower alkyl having 1 to 4 carbon atoms, lower alkoxycarbonyl having 2 to 4 carbon atoms and lower alkylthio having 1 to 3 carbon atoms said substituents being present on the ring carbon atoms thereof, and ••••••• signifies a single bond or a double bond, or a pharmacologically acceptable salt thereof.

2. A compound according to claim 1, wherein n is 2.

3. A compound according to claim 1, wherein ••••••• is a single bond.

4. A compound according to claim 1, wherein ••••••• is a double bond.

5. A pharmaceutical composition which comprises a pharmaceutically effective amount of a compound or pharmacologically acceptable salt thereof as defined in claim 1 and a pharmaceutically acceptable carrier therefor.

6. A pharmaceutical composition according to claim 5 effective as a therapeutic agent for diabetes mellitus or hyperlipidemia.

* * * * *